US010285636B2

(12) United States Patent
Singer

(10) Patent No.: US 10,285,636 B2
(45) Date of Patent: May 14, 2019

(54) APPARATUS AND METHOD FOR DETECTING BRUXISM

(71) Applicant: Brian Singer, Armonk, NY (US)

(72) Inventor: Brian Singer, Armonk, NY (US)

(73) Assignee: Half Mile Technologies, Inc., Armonk, NY (US)

( * ) Notice: Subject to any disclaimer, the term of this patent is extended or adjusted under 35 U.S.C. 154(b) by 91 days.

(21) Appl. No.: 15/353,464

(22) Filed: Nov. 16, 2016

(65) Prior Publication Data

US 2017/0135626 A1 May 18, 2017

Related U.S. Application Data

(60) Provisional application No. 62/256,087, filed on Nov. 16, 2015.

(51) Int. Cl.
*A61B 5/0488* (2006.01)
*A61B 5/00* (2006.01)
*A61B 5/0476* (2006.01)
*A61B 5/11* (2006.01)
*G06T 7/00* (2017.01)

(52) U.S. Cl.
CPC ......... *A61B 5/4557* (2013.01); *A61B 5/0476* (2013.01); *A61B 5/0488* (2013.01); *A61B 5/1128* (2013.01); *G06T 7/0016* (2013.01); *A61B 2576/02* (2013.01); *G06T 2207/10016* (2013.01); *G06T 2207/10024* (2013.01); *G06T 2207/30036* (2013.01)

(58) Field of Classification Search
CPC combination set(s) only.
See application file for complete search history.

(56) References Cited

U.S. PATENT DOCUMENTS

| 2009/0291417 | A1 | 11/2009 | Rubbert et al. |
| 2011/0066066 | A1 | 3/2011 | Van Kemenade et al. |
| 2012/0115107 | A1 | 5/2012 | Adams |
| 2012/0203133 | A1 | 8/2012 | Jadidi |
| 2013/0006150 | A1* | 1/2013 | Suzuki ................ A61B 5/4557 600/586 |
| 2014/0085449 | A1 | 3/2014 | Mandelis et al. |
| 2016/0095570 | A1* | 4/2016 | Allessie ............... A61B 5/4557 600/301 |
| 2017/0325910 | A1* | 11/2017 | Salah ................... A61C 7/002 |

FOREIGN PATENT DOCUMENTS

CN          1810319 A    8/2006

* cited by examiner

*Primary Examiner* — Janese Duley
(74) *Attorney, Agent, or Firm* — Oblon, McClelland, Maier & Neustadt, L.L.P.

(57) ABSTRACT

Described herein is an apparatus and method of detecting bruxism. The method includes the steps of: capturing a video of a subject, performing by circuitry included in the apparatus, spatial filtering of each image frame included in the captured video. Further, the method includes generating by circuitry, a filtered image by temporally filtering the spatially filtered image frames, the temporally filtered image including data belonging in a first frequency range, and wherein a subset of data is associated with a predetermined color variation to indicate presence of bruxism in the subject.

4 Claims, 7 Drawing Sheets

APPARATUS AND METHOD FOR DETECTING BRUXISM

CROSS-REFERENCE TO RELATED APPLICATIONS

This application is based upon and claims the benefit of priority to provisional U.S. Application No. 62/256,087, filed Nov. 16, 2015, the entire contents of which are incorporated herein by reference.

BACKGROUND

Field of Disclosure

Embodiments described herein generally relate to a device and a corresponding method of using the device to detect bruxism.

Description of Related Art

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Bruxism is a disorder in which a person excessively grinds or clenches his/her teeth. Bruxism symptoms typically include tooth wear, headaches, back pain, and neck pain. The most common method of treating bruxism is through the use of a mouth-guard. However, the mouth-guard does not cure bruxism, but rather only prevents the symptom of tooth wear. As such, several researchers have attempted to reduce bruxism through bio-feedback systems. However, bio-feedback devices such as intra-oral pressure sensors, and Electromyography (EMG) based systems are intrusive to wear, and cause the patient discomfort.

Accordingly, there is a requirement for a device that accurately detects bruxism in a non-intrusive manner.

SUMMARY

An aspect of the resent disclosure provides for a method of detecting bruxism, the method including the steps of: capturing a video of a subject; performing by circuitry, spatial filtering of each image frame included in the captured video; and generating by circuitry, a filtered image by temporally filtering the spatially filtered image frames, the temporally filtered image including data belonging in a first frequency range, and wherein a subset of data is associated with a predetermined color variation to indicate presence of bruxism in the subject.

By one embodiment of the present disclosure is provided an apparatus for detecting bruxism. The apparatus includes circuitry configured to capture a video of a subject; perform spatial filtering of each image frame included in the captured video; and generate a filtered image by temporally filtering the spatially filtered image frames, the temporally filtered image including data belonging in a first frequency range, and wherein a subset of data is associated with a predetermined color variation to indicate presence of bruxism in the subject.

According to one embodiment of the present disclosure is provided a non-transitory computer readable medium having stored thereon a program that when executed by a computer causes the computer to execute a method of detecting bruxism, the method including the steps of: capturing a video of a subject; performing by circuitry, spatial filtering of each image frame included in the captured video; and generating by circuitry, a filtered image by temporally filtering the spatially filtered image frames, the temporally filtered image including data belonging in a first frequency range, and wherein a subset of data is associated with a predetermined color variation to indicate presence of bruxism in the subject.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments of this disclosure that are proposed as examples will be described in detail with reference to the following figures, wherein like numerals reference like elements, and wherein.

DETAILED DESCRIPTION OF EMBODIMENTS

Figure 1:
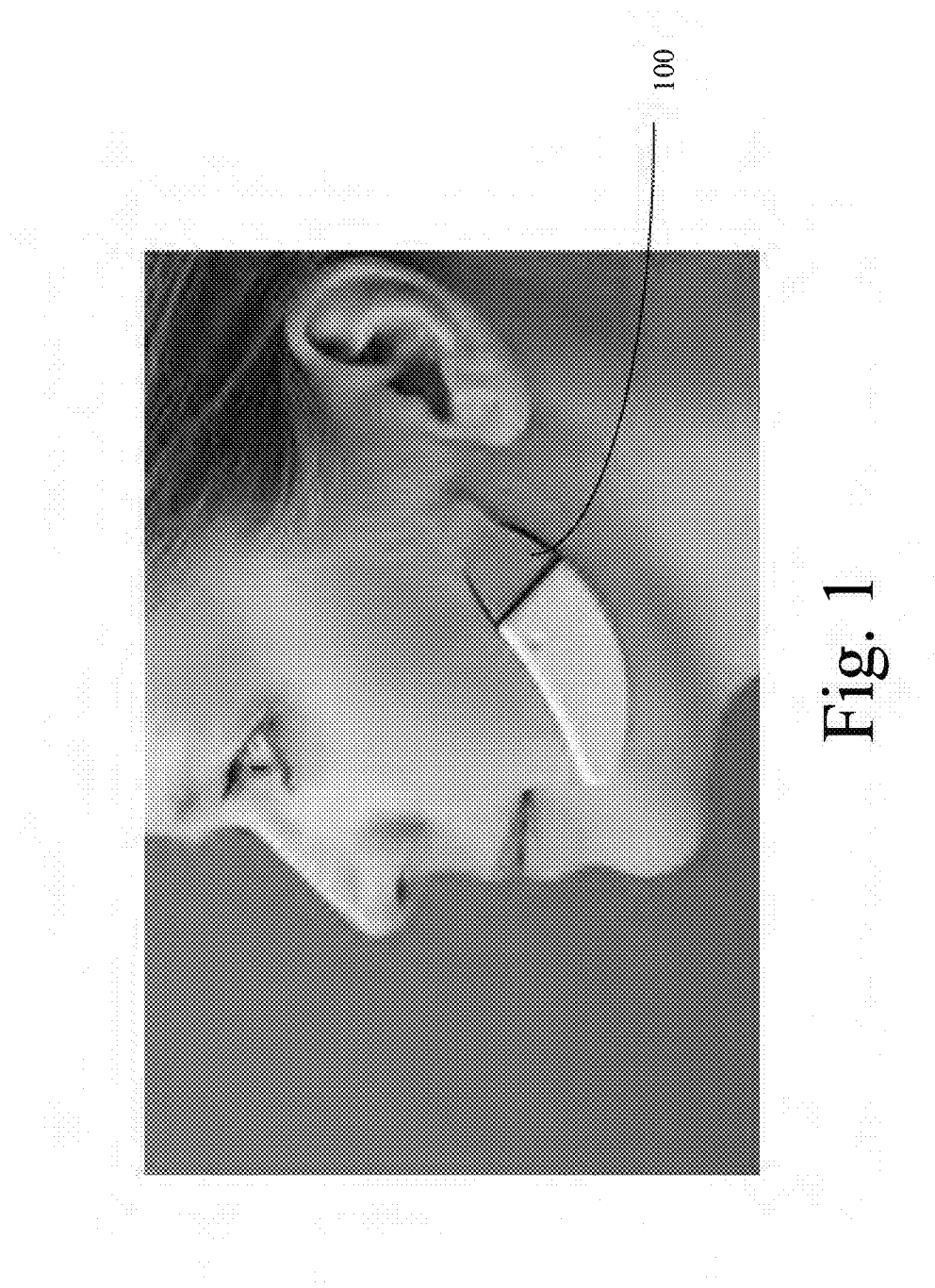
FIG. 1 illustrates an exemplary electromyography based device to detect bruxism.

Referring now to the drawings, wherein like reference numerals designate identical or corresponding parts throughout the several views. Accordingly, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

Bruxism is the act of excessively grinding teeth and/or clenching the jaw. Bruxism may occur during the day referred to as 'awake bruxism', or while the patient is asleep referred to as 'sleep bruxism'. Approximately 20% of the adult population has awake bruxism, and 8-16% of the adult population is estimated to have sleep bruxism. Of these percentages, it is estimated that only 20-30% have been diagnosed. The current standard treatment for bruxism is a mouth guard. However, a mouth guard does not actually cure bruxism, but it only prevents the symptom of tooth wear.

Both the masseter and temporalis muscles contract when bruxing. These muscles exert force on the surrounding tissue when a patient bruxes, leading to headaches, neck pain, and back pain. Around 80% of all bruxism episodes are silent, thereby making it difficult to detect bruxism without an intraoral device.

According to one embodiment of the present disclosure, bruxism symptoms can be separated into three groups: tooth, joint, or muscle related issues. Tooth symptoms include excessive wear and frequent fractures of dental restorations, joint symptoms involve temporomandibular disorders (TMD), and muscle symptoms involve pain in back and neck muscle groups, and in the temporalis muscle. The majority of patients that report back and neck pain go to a physical therapist before any teeth wear is apparent. However, it is usually difficult for the physical therapist to make a diagnosis for bruxism because most of their patients are either unaware that they clench, or they have sleep bruxism. Similarly, a dentist may have difficulty diagnosing a patient with bruxism efficiently because the dentist must first rule out other issues, such as improper mouth fillings, which may cause similar symptoms.

After a patient has been diagnosed with bruxism, the condition remains difficult to treat effectively. The usage of a mouth guard is sacrificial as patients wear down the plastic guard instead of their teeth. Mouth guards prevent teeth related symptoms effectively but do not help the muscle and/or joint related symptoms. Furthermore, the mouth guard does not cure bruxism. Accordingly, bio-feedback systems have been created to cure bruxism. For instance, one study treated sleep bruxism with a bio-feedback system by waking the subject up every time he or she bruxed. Although the system lowered the occurrence of bruxism, the user faced considerable sleep deprivation. Alternatively, bio-feedback systems have been used to treat awake bruxism. One method for creating bio-feedback systems is through the use of intraoral devices such as the intra-splint force detector, which detects the jaw force exerted on a splint. Such a device claims a 50% success rate, but was observed to fail due to long-term exposure to the static forces normally exerted between the teeth. Alternatively or in addition to the above described bio-feedback systems, techniques of treating bruxism include the release of a taste stimulus when a user bruxes. However, a major drawback of such bio-feedback systems is that the bio-feedback devices/ techniques are far too intrusive for the user, and moreover have to be placed inside of the mouth of the user which may lead to further discomfort.

Turning to FIG. 1, there is provided an exemplary electromyography (EMG) based device 100 to detect bruxism. EMG-based devices use electrodes that are placed directly on one of the jaw muscles to detect bruxism. Most products based on this technology, including Bite Strip™ (device 100 as shown in FIG. 1), are placed on the masseter muscle. When the masseter muscle contracts, an electrical potential is detected using an electrode. However, the EMG based devices incur the following disadvantages: a) they require the electrodes to be placed directly on the jaw muscles; b) they are, therefore, conspicuous to wear; c) the muscle is already contracted by the time it is possible to obtain an electrical signal from the muscle; and d) they must have low sensitivity to reduce false positives during normal jaw muscle activity, which makes them useful only for heavy bruxers.

According to one embodiment of the present disclosure, there is provided an electroencephalogram (EEG)-based device for detecting the onset of bruxism. In contrast to the EMG-based devices, EEG systems are designed to detect a variety of stimuli using algorithms that identify spatial and temporal patterns in neuronal firing. An EEG-based system allows for the electrodes to be placed on the head rather than the muscle, making it possible for a less intrusive device. The spatial algorithms treat the brain holistically, combining data from all of the electrodes to predict a stimulus. Further, Independent Component Analysis (ICA) techniques have been implemented that use cross correlation between electrode data to determine which electrodes most directly contribute to registering a particular stimulus. Once a selective subset of electrodes is chosen, only EEG data from those electrodes is used to predict that stimulus.

According to one embodiment, there is provided an Eulerian Video Magnification technique that analyzes temporal variations (of motion or color) in video. Magnifying the temporal variations enables the naked eye to observe otherwise invisible changes in the video. The algorithm first applies a spatial filter to each frame in the video. Depending on the application, various spatial frequencies are filtered out of each frame. The process has the effect of removing edges and other details that are not important. Next a temporal filter is applied to the series of spatially filtered frames. The process extracts certain movements or color changes in the desired frequency range of the video. The EVM algorithm then magnifies the motion or color in the temporally filtered frames by multiplying the individual pixel values of the temporally filtered image by an arbitrary alpha value, and adds the resulting image to the original video image. The result is a video in which the color or motion of interest is enhanced to be visible by the naked eye.

In what follows is described an EEG and an EVM-based device that are utilized to detect bruxism. Both the devices provide a less intrusive method for detecting bruxism as compared to the devices used thus far for bruxism detection purposes. In the EEG based device, the use of only a single electrode is described for bruxism detection. Such a device is a non-intrusive technique of detecting bruxism. Moreover, an EVM-based bruxism detection technique is described that provides a completely non-intrusive and non-contact mechanism of detecting bruxism, as the user does not have to wear any device at all in this case to detect bruxism. The ability to detect bruxism allows for both a bruxism diagnosis and treatment device.

Figure 2:
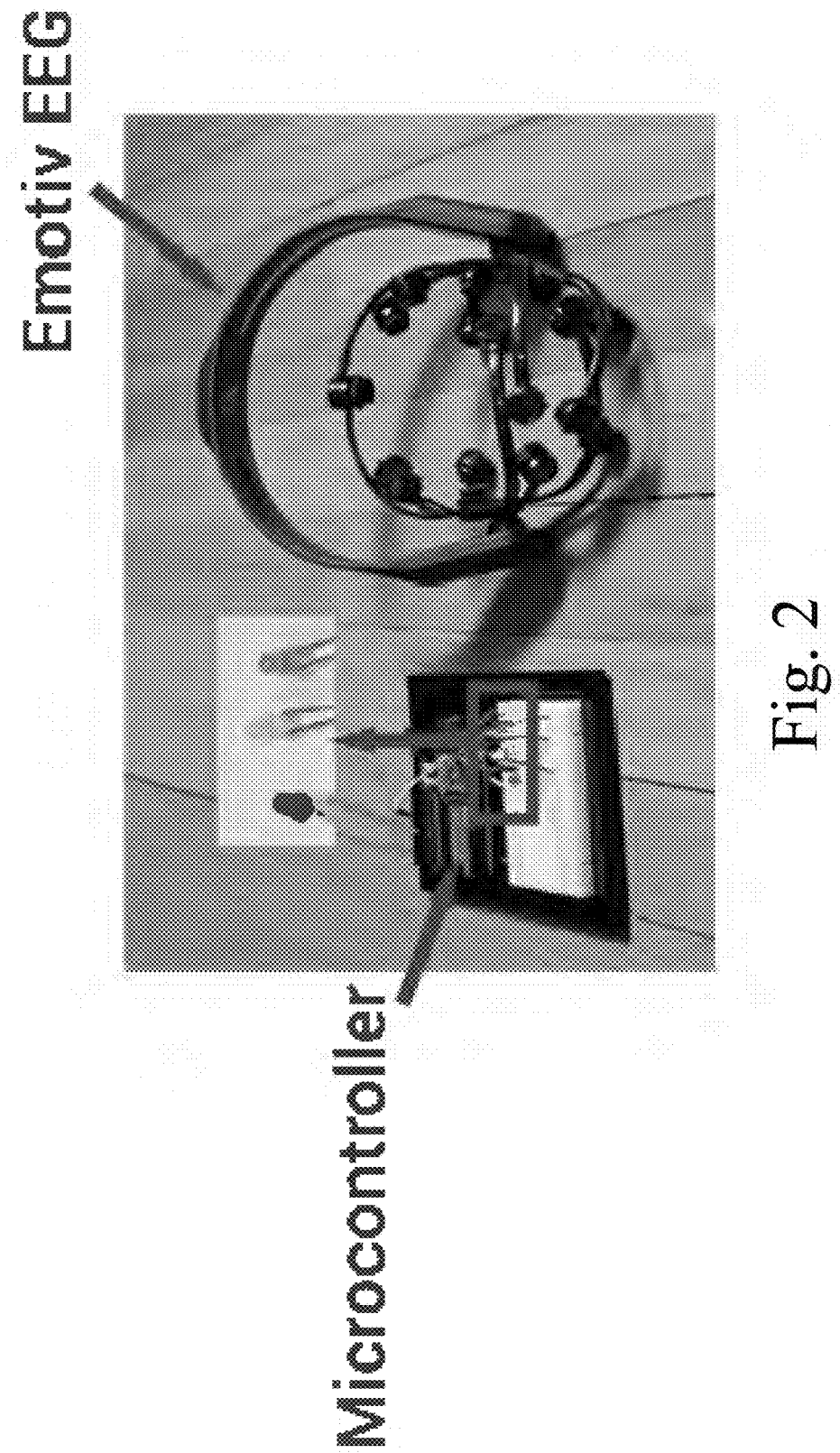
FIG. 2 illustrates according to one embodiment an EEG data collection system.

By one embodiment, an EEG-based device detects the onset of bruxism using EEG data. As EEG detects the electrical activity in the brain, a properly designed EEG device detects the onset of bruxism before the subject actually tightens the jaw muscles. A first phase in detecting bruxism by an EEG based device is data acquisition. In order to process and analyze EEG data, software such as MATLAB can be utilized to load and parse huge EEG datasets. FIG. 2 depicts a hardware configuration according to one embodiment, which is utilized to collect EEG data. For instance, as shown in FIG. 2, the hardware can include a headset (e.g., an Emotiv EEG EPOC headset) to collect all of the EEG data for this study. The Emotiv EEG headset is a wireless Bluetooth device that collects and sends EEG data to a computer with a sampling frequency of 128 Hz. The Emotiv Test Bench Software can be successfully utilized to create CSV files that include the EEG data from each of the electrodes.

Further, a classifier is designed that enables bruxism detection. A "classifier" in the machine learning literature refers to an algorithm that categorizes data based upon a set features extracted from the data. For instance, by one embodiment, the categories of "bruxing-data" and "not bruxing data" are used to classify the collected data. Classifiers extract certain features from the data. Further, a classifier is trained on actual data to distinguish between the categories. In order to train the classifier, a system is required to indicate to the test subject, as to when should the subject brux and when should the subject relax, while simultaneously collecting EEG data from the subject. As such, the hardware setup as shown in FIG. 2 is used to collect data. The setup includes: a) an Emotiv EEG headset that collects data and wirelessly transmits it to a laptop; b) a microcontroller such as an Arduino Uno microcontroller that is wired to a series of LEDs, which illuminated to act as a stimulus to the test subjects; and c) a software processing portion e.g., the Emotiv Test Bench Software that streams the EEG data to a file. In addition to lighting the LEDs, the microcontroller simultaneously transmits a marker over a serial connection to the data file, indicating the applied stimulus.

As shown in FIG. 2, the microcontroller system is configured with one green, one yellow, and one red LED indicator. First, either a green or yellow LED is turned on. In order to prevent the subject from being able to predict when the stimulus indicating "clench" would arrive, the timing between LED illuminations is randomly selected using a random number generator. The green LED signals the subject to clench their jaws, while the Yellow LED signals the user to not clench. By one embodiment, the subject continues the given task until they observe a red LED stimulus. After a small time-out period, the entire process restarts. While conducting the test: a) clench operation is programmed to last a random duration between five and eight seconds, b) the rest periods are programmed to last a random duration between five and eight seconds, c) the microcontroller is programmed to randomly indicate to the subject to either clench (green LED) or not clench (yellow LED); and e) the process is repeated until data is collected for a predetermined number of clench operations, e.g., 20 clenches. By one embodiment, multiple datasets are collected and used to train and debug a classification system, which is used to process the EEG data to identify the onset of bruxism.

Figure 3:
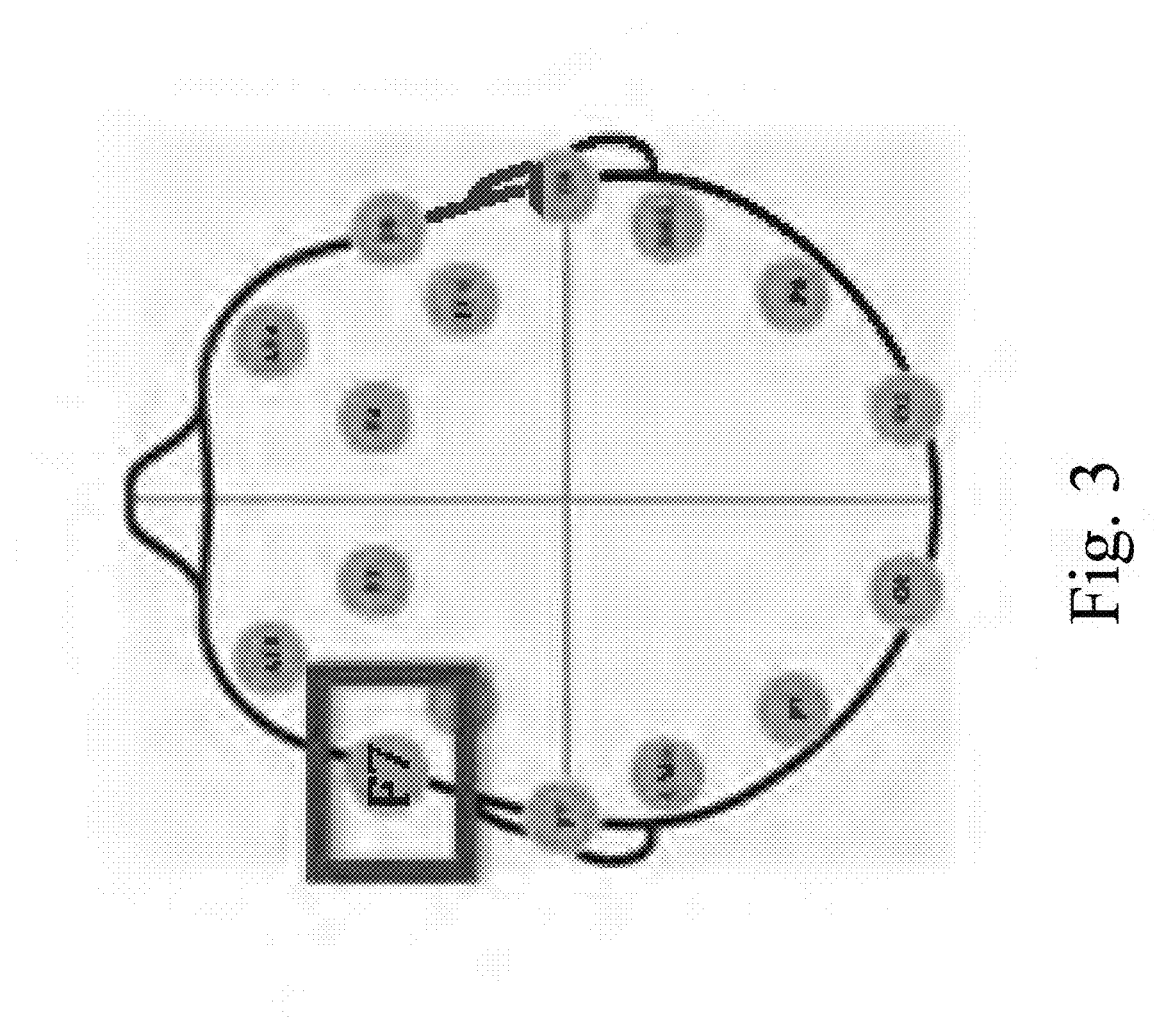
FIG. 3 illustrates an exemplary electrode map according to one embodiment.

By one embodiment, in order to reduce the total number of required electrodes, it is necessary to determine mathematically, which electrodes are the most important for detecting bruxism. Such electrodes pick up the data that is most relevant for discriminating between the cases of clench and no clench. By one embodiment, an Independent Component Analysis (ICA) algorithm is used on the previously collected EEG data of bruxism to determine the useful electrode. The ICA algorithm cross-correlates the EEG-data from all of the electrodes. The ICA algorithm reduces the electrical noise in each electrode created by other areas of the brain. The resulting signals demonstrate which electrode's signal contributes most to the measured EEG response. As shown in FIG. 3, it is observed that the data from electrode F7 is most correlated with the EEG response during bruxing.

Figure 4:
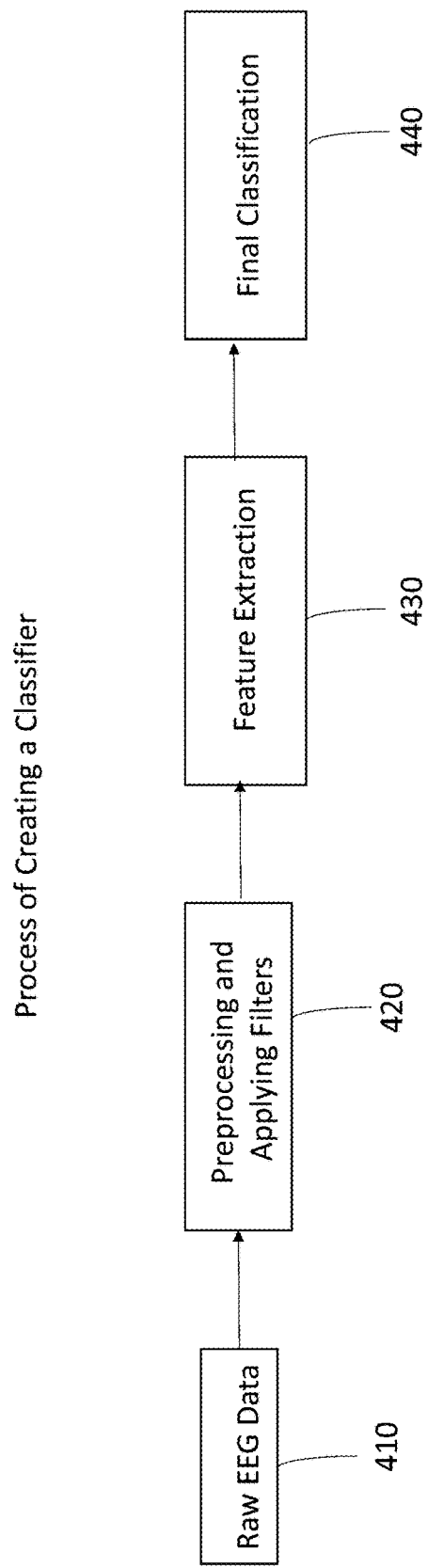
FIG. 4 illustrates an exemplary flowchart depicting the steps performed to create a classifier.

FIG. 4 illustrates an exemplary flowchart depicting the steps performed to create a classifier. The classifier processes data and groups data into categories in a statistical manner. By one embodiment, a modified linear discriminant analysis function is used as a classifier. As shown in FIG. 4, the first step is to train the classifier using data collected from a subject for which the bruxism results are known. The training algorithm takes the raw EEG data and identifies important features in the stimulus for classifying bruxism. As shown in FIG. 4, the process for creating the classification include the steps of: 1) import the EEG data files (step 410) and select the electrode to be analyzed, 2) use software to preprocess and apply filters (step 420), 3) create a function using a combination of the bruxism-discriminating data features from the EEG datasets (step 430); and 4) test the final classification by processing EEG data in real-time (step 440).

By one embodiment, MATLAB software script is used to process the data. The data corresponding to the EEG data is loaded from CSV files. Each column in the CSV file represents the data from a single electrode. The final column includes the markers indicating whether or not a visual stimulus is present. The markers are written to the data file by the microcontroller based upon the presented stimulus (a green or yellow light). Although the Emotiv EEG has 14 electrodes, by one embodiment of the present disclosure, only the F7 electrode (as shown in FIG. 3) is used for the classification process, as any practical implementation would need to be minimally intrusive to the user. Accordingly, it is envisioned that a single electrode device could be easily manufactured and used as a noninvasive biofeedback device to cure or reduce bruxism.

Preprocessing the EEG data organizes the datasets for the classification by extracting specific pieces of the data where the stimuli occurred. The MATLAB script first locates all of the markers and selects the EEG data from the chosen electrode surrounding each marker. A specific marker value indicates when the subject clenches, and another value signifies when the subject does not clench. The MATLAB script separates each of datasets into two classes: positive (clench) and negative (no clench). In order to avoid over fitting the data, the script randomly selects half of the datasets in each group for training the classifier and the other half of the datasets are used to test the final classification. After preprocessing the data, the script applies basic noise filters to the EEG data. The first filter applied is a five-point moving average filter. Such a filter smooths the data by averaging each point with the four previous values. Next, the data is normalized by applying a mean offset.

It must be appreciated that the data collected from the Emotiv is the electrical brain activity in the time domain. The classifier converts the data into the frequency domain using a Fast Fourier Transform (FFT) algorithm. Note that there are six bands of electrical frequencies generally associated with brain activity: delta (0-4 Hz), theta (4-7 Hz), alpha (7-14 Hz), beta (15-30 Hz), and gamma (30-100 Hz). The classification takes the average magnitude of all points within each frequency range bin and transmits the information to the classifier.

By one embodiment, the classifier is a modified step-wise discriminant analysis algorithm. Using the first half of the collected data, each of the frequency points in group 1 (the clench group), and each of the frequency points in group two (the no clench group) are aligned and used to train a classifier. The resulting classifier is a multidimensional function. The function uses a set of frequency points, and returns a number between zero and one. A zero corresponds to the no clench classification, while a one corresponds to the clench classification. A threshold between zero and one is selected to group each data set into a particular classification. For instance, a threshold of 0.5 may be chosen. However, the sensitivity of the classification can be tuned by adjusting the threshold. Once the training is complete, the classifier is tested by applying it to the second half of the collected data.

By one embodiment, only one feature (i.e., magnitude of a single frequency component) is utilized by the classifier. Specifically, each and every frequency component is analyzed to create an individual classifier, test each classifier against the second half of the data, and grade all the classifiers based on how well each performed. Based on the grade received, the point that predicted the most number of clenches correctly is determined as the first feature. The classification then repeats the process using the previously selected feature in every discriminant analysis function. If adding any new points in combination with this original feature indicates an improvement in predication, the point is added to the selected features and the process is repeated. Note however, that if there is no improvement in the prediction, the classification is finalized and the set of features is stored in the classification.

By one embodiment, the classifier can be tested offline on an initial test subject by performing an experiment. During the experiment, the subject is required to perform the clench operation, wherein a video camera records the process. For instance, in one experiment, the subject clenches 20 times, and does not clench 20 times for each dataset. The EEG data is then processed with the classifier in an attempt to determine whether the subject bruxed during the trial. While reviewing the video recording it may be difficult to determine when the subject was clenching or not clenching, even during the conscious clenching dataset. Thus, independent verification of the data may be cumbersome. Based on the initial testing, the test procedure can be improved and used as described later.

By one embodiment, upon reviewing the initial video footage from the EEG testing, it is observed that there is a subtle and barely-noticeable movement in the masseter muscle during bruxing. Accordingly, in what follows is described a technique of implementing Eulerian video magnification (EVM) to process the video data to enhance the motion, in order to create a noncontact, noninvasive method of detecting bruxism.

Figure 5:
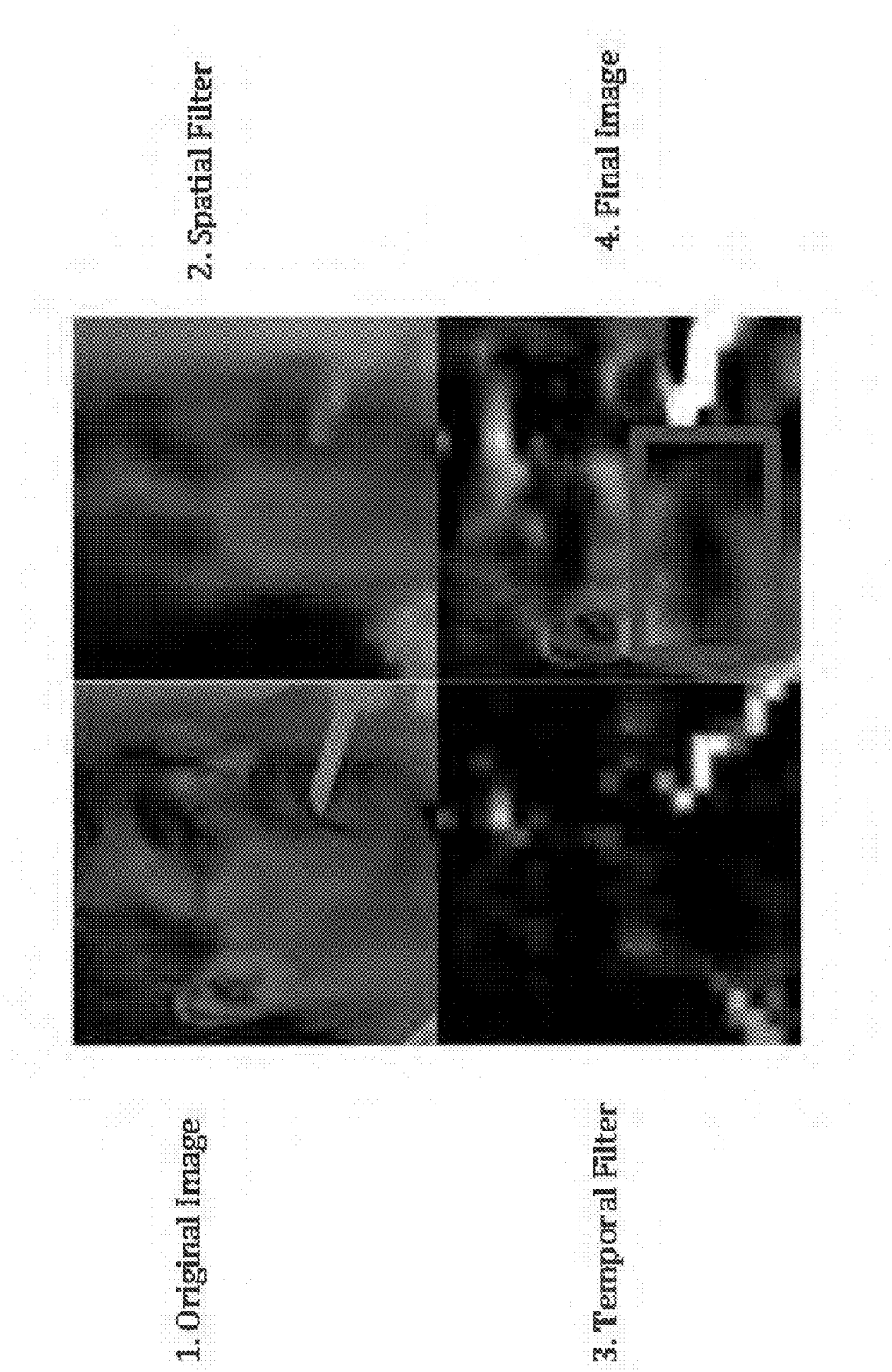
FIG. 5 depicts an exemplary sequence of images depicting the step of Eulerian video magnification (EVM) being applied to detect bruxism.

Turning to FIG. 5 is depicted is an exemplary real-time implementation of EVM to detect bruxism. As shown in FIG. 5, EVM is applied to each frame in a captured video. First, a spatial filter is applied. The spatial filter blurs and downsizes the image, for example, to a 20×20 pixel square. It must be appreciated that the downsampling process reduces the data rate i.e., reduces the size of the overall data, thereby resulting in useful data that may be used to detect bruxism. Moreover, downsampling reduces the signal-to-noise ratio.

After down-sampling the image (i.e. each frame of the captured video), two Infinite impulse Response (IIR) temporal filters are applied. The first IIR temporal filter is a low pass filter, which cuts off specified low frequencies that are not of interest. Further, the second filter being applied is a high pass temporal filter, which cuts off specified high frequencies that are also not of interest. It must be appreciated that any type of high-pass/low-pass temporal filter(s) may be used from the rich literature on filtering techniques.

Further, for each frame, the low pass frequency filtered image data is subtracted from the high pass frequency filtered image data to obtain a difference image which indicates information about mandible/masseter muscle motion in relation to bruxism. The computed difference image is multiplied by an alpha factor (referred to herein as a magnification level). By one embodiment, the difference image depicts data corresponding to muscle motion only in a certain frequency range. For instance, muscle motion may be computed only in the frequency range of 0.05 Hz to 3 Hz. By one embodiment, a frequency range of 0.05 to 10 Hz may be selected for obtaining the masseter muscle motion. However, a preferable range of frequency for obtaining the masseter muscle motion is 0.1 Hz to 1.5 Hz.

Thereafter, the 20×20 filtered images are up-sampled to be the same size as the original image. By the above described technique, a level of darkness is added to each pixel in response to motion in the frequency band chosen to detect bruxism i.e., as shown in FIG. 5, pixels showing mandible/masseter muscle motion are black, and other pixels remain the same color. Moreover, the up-sampled image can further be overlaid on the original captured image to provide a visual depiction of bruxism.

By one embodiment of the present disclosure, upon down-sampling the captured images, the images may be processed by a single temporal band-pass filter (instead of a combination of a low pass and high pass temporal filter) in order to extract masseter muscle motion in the certain desired frequency range. Note that in the band-pass frequency range, pixels upon being temporally filtered show color value variations. Accordingly, based on a predetermined threshold, when the color value variation of a certain pixel exceeds the threshold, the corresponding pixel may be determined to indicate bruxism. On the other hand, when the color variation of the pixel is lower than the predetermined threshold, a processor (described later with reference to FIG. 6) included in a bruxism detection device may determine that the corresponding pixel is not indicative of bruxism. Furthermore, it must be appreciated that instead of processing the entire capture image frame, the spatial-temporal filtering may be achieved by selecting a predetermined portion(s) of the frame, and employing the above described techniques only to the selected portion(s) to detect bruxism. Note that in this aspect, the bruxism detection device incurs the advantageous ability of reducing a processing complexity of the processor. Furthermore, it is recognized that selecting a portions(s) of the image and aggregating information about the pixels in that portion is equivalent to spacial filtering as disclosed in present disclosure.

Figure 6:
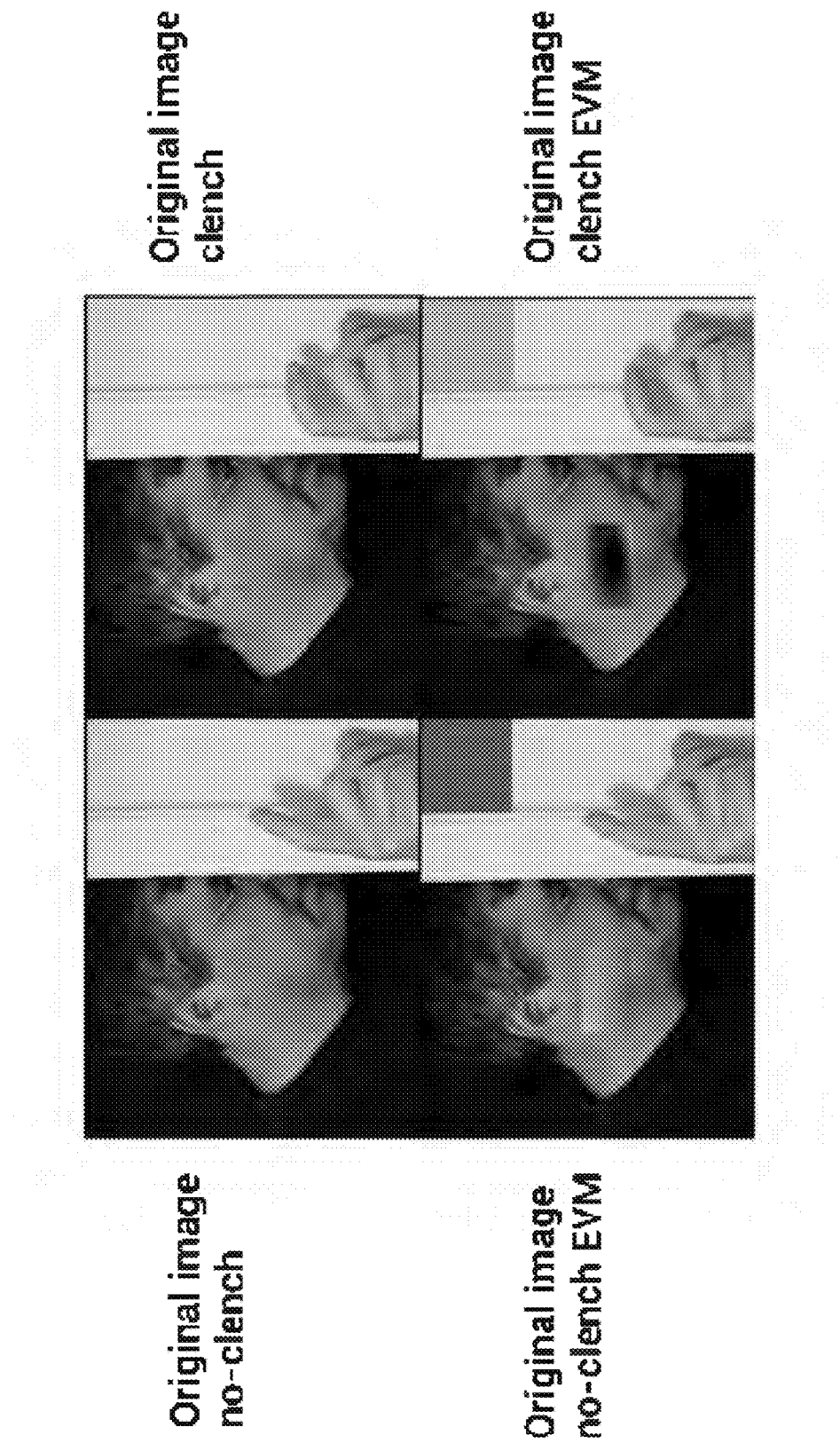
FIG. 6 depicts an exemplary comparison of bruxism detection between an original image and an image generated by Eulerian magnification.

By one embodiment, in order to determine whether the subject is bruxing or not, the pixel coordinates of a region (in this example, a rectangle) can be set to the jaw area around the masseter muscle. This area reveals the most movement when a user bruxes. Furthermore, by one embodiment, the algorithm calculates the average pixel intensity in the rectangle (shown in FIG. 6). Specifically, FIG. 6 depicts a comparison of bruxism detection between an original image and the images with EVM applied to the area around the masseter muscle. Note that the subject indicated clenching by lowering his index finger. The red and green indicators are applied to the video image by processing software to depict no clenching and clenching operation being performed. Moreover, the head of the subject is manually stabilized to avoid facial tracking which would be part of a future upgrade. By one embodiment, if the average pixel density falls below a set threshold, then it indicates that the subject is clenching. Both the threshold and alpha (magnification level) may be adjusted to determine the final sensitivity of the algorithm.

By one embodiment, the performance of the above described EEG classification and Eulerian Video Magnification classification for detecting bruxism is each compared to Bite Strip™. In the experiment performed for determining the performance of each bruxism technique, Bite Strip™ is placed on the masseter muscle and an LED flashes when it believes the subject is clenching. The experiment was conducted on three subjects: subject A and B are both males, while subject C is a female. Although none of the subjects had been previously diagnosed with bruxism, the devices analyzed activation of jaw muscle movement (clenching) which is essentially bruxism. For each device the subjects were first given a tooth protector (e.g., a popsicle stick) on which to bite to protect their teeth. An audio recording instructed the subject to clench and release their teeth 25 times. The device's output were then recorded analyzed. The subjects were further instructed to repeat the process without having a tooth protector on which to bite. The tooth protector induced each subject to bite harder (simulating heavy bruxism) while protecting their teeth. Without the tooth protector, subjects were not able to bite as hard, simulating only medium to light bruxism.

A performance evaluation of the above experiment is depicted below in Table I. The Bite Strip™ performs well for heavy bruxism (96% accuracy) but is less reliable when subjects clenches without a tooth protector in their mouth (9.3% accuracy).

TABLE I number of clenches each bruxism detection device is able to correctly predict.

| Subject | Bite Strip ™ | | EEG | | EVM | |
|---|---|---|---|---|---|---|
| | Tooth protector | No Tooth protector | Tooth protector | No Tooth protector | Tooth protector | No Tooth protector |
| A | 23/25 (92%) | 3/25 (12%) | 24/25 (96%) | 23/25 (92%) | 25/25 (100%) | 25/25 (100%) |
| B | 24/25 (96%) | 2/25 (8%) | 24/25 (96%) | 23/25 (92%) | 21/25 (84%) | 22/25 (88%) |
| C | 25/25 (100%) | 3/25 (8%) | 25/25 (100%) | 22/25 (88%) | 23/25 (92%) | 23/25 (92%) |
| Average | 96% | 9.3% | 97.3% | 90.6% | 92% | 93.3% |

The EEG-based bruxism detection performs well for all subjects with or without the tooth protector (97.3% and 90.6% accuracy respectively). The EVM algorithm performs well for the all subjects with or without the tooth protector (92% and 93.3% accuracy respectively).

By one embodiment, data obtained from the above-described techniques is interpreted by implementing a two-proportion z-test. It is observed that there is statistically no significant difference between the Bite Strip™ detection rate and the EEG detection rate for clenches with the tooth protector (p=0.65). Similarly, it is observed that there is no statistical significant difference between the Bite Strip™ detection rate and the EVM detection rate for clenches with the tooth protector (p=0.30).

However, for the clenches without the tooth protector, there is a statistical significant difference between Bite Strip™ detection rate and EEG detection rate (p=4.26*10^-24). For the clenches without the tooth protector, there is a significant difference between Bite Strip™ and EVM (p=7.7*10^-25). On average, all three devices statistically had nearly identical accuracy while the subject used the tooth protector. However, the Bite Strip™ device has poor accuracy when the user did not bite on the tooth protector. Moreover, the subjects indicated that when using the tooth protector they were able to clench much more firmly. The Bite Strip™ device is designed for heavy clenches and filters out the electrical activity associated with other jaw muscle movements. For this reason, the Bite Strip™ device tends to filter out the softer clenching. Both the EEG-based classifier and the EVM algorithm perform better than the Bites Strip for softer clenches. Light to medium bruxism is more prevalent and harder to diagnose because tooth wear is less severe. For a total of 150 clenches, it is observed that an 8% margin of error is achieved when using a 95% confidence interval. For the EEG-based classifier to be less sensitive, the classifier can be trained to ignore moderate clenching. It must be appreciated that a change in the sensitivity for the EVM-based technique requires only a change in one or both of the alpha magnification value and/or the detection threshold that is applied.

Furthermore, it is recognized that while Bruxism was detected in this preferred embodiment by detecting color variations of certain frequencies in video, the EVM technique would be equally effective in detecting motion frequencies in video as an alternative means to detect bruxism.

By one embodiment, an artificial intelligent (AI) agent can be implemented to detect the presence of bruxism. The AI agent can include a classifier, which can be trained based on a known set of bruxism and non-bruxism related images (data) filtered according to the invention. Further, for a particular image frame (that has for instance, been down-sampled and temporally filtered), the classifier can determine whether the image is a bruxism indicating image or a non-bruxism indicating image. By one embodiment, the classifier may group pixels in a certain region and compute an average pixel intensity corresponding to the group of pixels. Further, the computed average pixel intensity may be compared to a predetermined pixel intensity threshold. Based on the computed average pixel intensity exceeding the threshold, the AI agent or some other algorithm can determine the presence of the bruxism.

Each of the functions of the described embodiments may be implemented by one or more processing circuits. A processing circuit includes a programmed processor (for example, processor 903 in FIG. 7), as a processor includes circuitry. A processing circuit also includes devices such as an application-specific integrated circuit (ASIC) and circuit components arranged to perform the recited functions.

Figure 7:
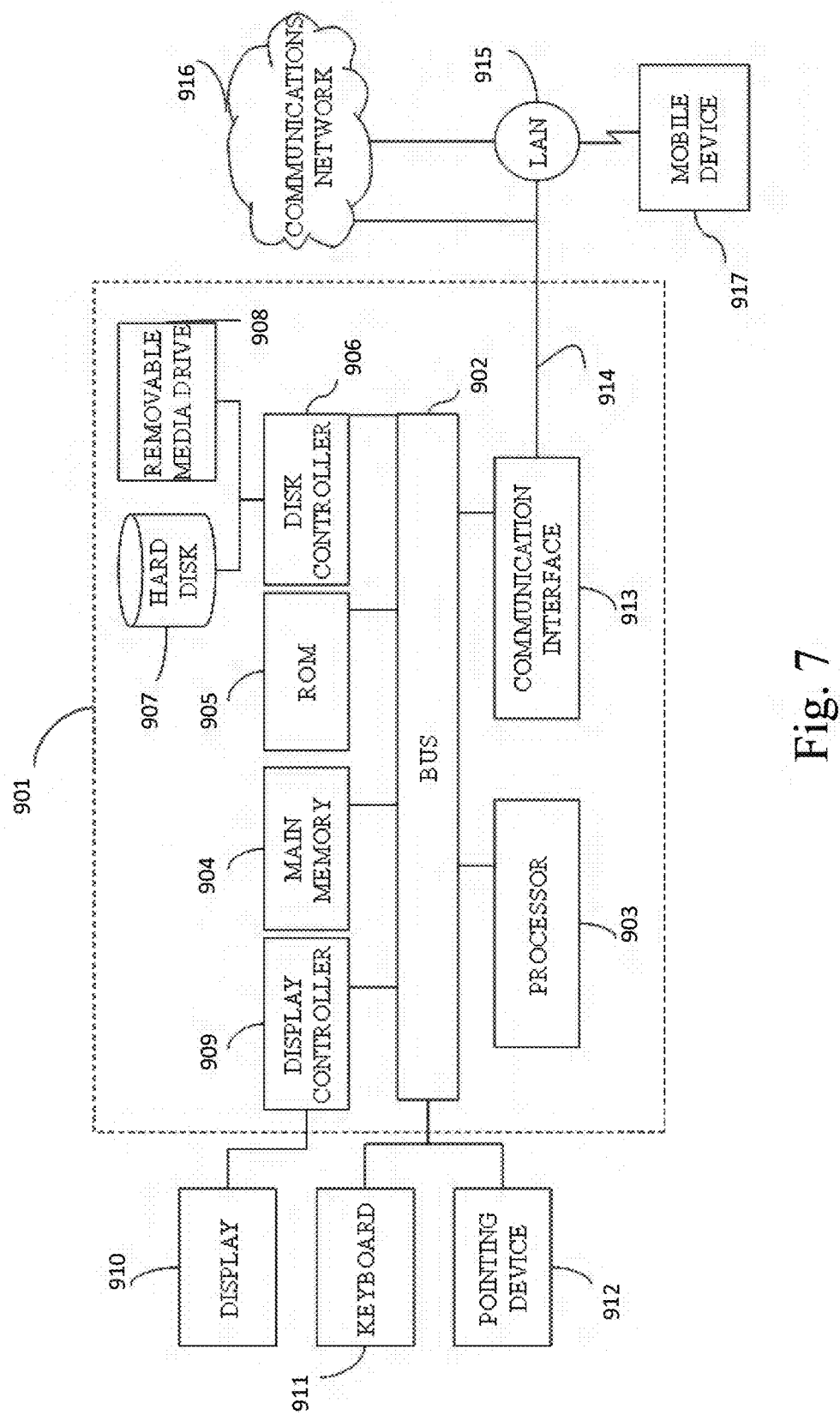
FIG. 7 illustrates a block diagram of a computing device according to one embodiment.

The various features discussed above may be implemented by a computer system (or programmable logic). For instance, the bruxism detection devices described herein may include processing circuitry that is configured to perform the functions of the above described embodiments. FIG. 7 illustrates such a computer system 901.

The computer system 901 includes a disk controller 906 coupled to the bus 902 to control one or more storage devices for storing information and instructions, such as a magnetic hard disk 907, and a removable media drive 908 (e.g., floppy disk drive, read-only compact disc drive, read/write compact disc drive, compact disc jukebox, tape drive, and removable magneto-optical drive). The storage devices may be added to the computer system 901 using an appropriate device interface (e.g., small computer system interface (SCSI), integrated device electronics (IDE), enhanced-IDE (E-IDE), direct memory access (DMA), or ultra-DMA).

The computer system 901 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 901 may also include a display controller 909 coupled to the bus 902 to control a display 910, for displaying information to a computer user. The computer system includes input devices, such as a keyboard 911 and a pointing device 912, for interacting with a computer user and providing information to the processor 903. The pointing device 912, for example, may be a mouse, a trackball, a finger for a touch screen sensor, or a pointing stick for communicating direction information and command selections to the processor 903 and for controlling cursor movement on the display 910.

The processor 903 executes one or more sequences of one or more instructions contained in a memory, such as the main memory 904. Such instructions may be read into the main memory 904 from another computer readable medium, such as a hard disk 907 or a removable media drive 908. One or more processors in a multi-processing arrangement may also be employed to execute the sequences of instructions contained in main memory 904. In alternative embodiments, hard-wired circuitry may be used in place of or in combination with software instructions. Thus, embodiments are not limited to any specific combination of hardware circuitry and software.

As stated above, the computer system 901 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 901, for driving a device or devices for implementing the invention, and for enabling the computer system 901 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 903 for execution. A computer readable medium may take many forms, including but not limited to, non-volatile media or volatile media. Non-volatile media includes, for example, optical, magnetic disks, and magneto-optical disks, such as the hard disk 907 or the removable media drive 908. Volatile media includes dynamic memory, such as the main memory 904. Transmission media, on the contrary, includes coaxial cables, copper wire and fiber optics, including the wires that make up the bus 902. Transmission media also may also take the form of acoustic or light waves, such as those generated during radio rave and infrared data communications.

Various forms of computer readable media may be involved in carrying out one or more sequences of one or more instructions to processor 903 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 901 may receive the data on the telephone line and place the data on the bus 902. The bus 902 carries the data to the main memory 904, from which the processor 903 retrieves and executes the instructions. The instructions received by the main memory 1904 may optionally be stored on storage device 907 or 908 either before or after execution by processor 903.

The computer system 901 also includes a communication interface 913 coupled to the bus 902. The communication interface 913 provides a two-way data communication coupling to a network link 914 that is connected to, for example, a local area network (LAN) 915, or to another communications network 916 such as the Internet. For example, the communication interface 913 may be a network interface card to attach to any packet switched LAN. As another example, the communication interface 913 may be an integrated services digital network (ISDN) card. Wireless links may also be implemented. In any such implementation, the communication interface 913 sends and receives electrical, electromagnetic or optical signals that carry digital data streams representing various types of information.

While aspects of the present disclosure have been described in conjunction with the specific embodiments thereof that are proposed as examples, alternatives, modifications, and variations to the examples may be made. Furthermore, it should be noted that, as used in the specification and the appended claims, the singular forms "a," "an," and "the" include plural referents unless the context clearly dictates otherwise.

The invention claimed is:

1. A method of detecting bruxism, comprising:
capturing a video of a face of a subject;
performing by circuitry, spatial filtering of each image frame included in an optical portion of the captured video; and
generating by the circuitry, a filtered image by temporally filtering the spatially filtered image frames of the optical portion of the captured video, the temporally filtered image including data belonging in a first frequency range that is within a subset of image frequencies associated with a predetermined color variation to optically detect clenching of muscles in the face that indicate presence of bruxism in the subject.

2. The method according to claim 1, wherein the subset of image frequencies is between 0.1 and 1.5 hertz (Hz).

3. The method according to claim 1, wherein the temporally filtered image uses a Eulerian Video Magnification technique for filtering the captured video.

4. A method of detecting bruxism, comprising:
capturing a video of a face of a subject;
performing by circuitry, spatial filtering and temporal filtering of each image frame included in an optical portion of the captured video; and
generating, by the circuitry, a filtered image based on the temporal filtering and spatial filtering, wherein the filtered image includes data belonging in a first frequency range that is within a subset of image frequencies associated with a predetermined color variation to optically detect clenching of muscles in the face that indicate presence of bruxism in the subject.

* * * * *